(12) United States Patent
Lerestif et al.

(10) Patent No.: US 6,982,350 B2
(45) Date of Patent: Jan. 3, 2006

(54) PROCESS FOR THE SYNTHESIS OF (1S)-4,5-DIMETHOXY-1-(METHYLAMINO METHYL)-BENZOCYCLOBUTANE AND ADDITION SALTS THEREOF, AND TO THE APPLICATION THEREOF IN THE SYNTHESIS OF IVABRADINE AND ADDITION SALTS THEREOF WITH A PHARMACEUTICALLY ACCEPTABLE ACID

(75) Inventors: Jean-Michel Lerestif, Yvetot (FR); Isaac Gonzalez Blanco, Toledo (ES); Jean-Pierre Lecouve, Le Havre (FR); Daniel Brigot, Saint-Marie-des-Champs (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/060,011

(22) Filed: Feb. 17, 2005

(65) Prior Publication Data

US 2005/0261376 A1    Nov. 24, 2005

(30) Foreign Application Priority Data

May 19, 2004  (FR) .................................... 04 05453

(51) Int. Cl.
*C07B 57/00*     (2006.01)
(52) U.S. Cl. ...................... 564/304; 564/338; 564/384

(58) Field of Classification Search ................ 564/304, 564/338, 384; 540/523
See application file for complete search history.

(56) References Cited

U.S. PATENT DOCUMENTS 5,013,760 A  *  5/1991  Farmer et al. ............... 514/649
5,296,482 A  *  3/1994  Peglion et al. .......... 514/212.06

FOREIGN PATENT DOCUMENTS

JP          04128270 A2  *  4/1992

* cited by examiner

*Primary Examiner*—Samuel Barts
(74) *Attorney, Agent, or Firm*—Hueschen and Sage

(57) ABSTRACT

Process for the synthesis of the compound of formula (I):

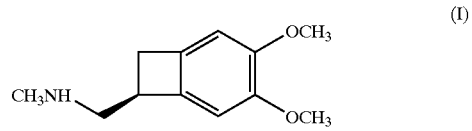

Application in the synthesis of ivabradine, addition salts thereof with a pharmaceutically acceptable acid, and hydrates thereof.

15 Claims, No Drawings

PROCESS FOR THE SYNTHESIS OF (1S)-4,5-DIMETHOXY-1-(METHYLAMINO METHYL)-BENZOCYCLOBUTANE AND ADDITION SALTS THEREOF, AND TO THE APPLICATION THEREOF IN THE SYNTHESIS OF IVABRADINE AND ADDITION SALTS THEREOF WITH A PHARMACEUTICALLY ACCEPTABLE ACID

The present invention relates to a process for the synthesis of (1S)-4,5-dimethoxy-1-(methylaminomethyl)-benzocyclobutane and addition salts thereof, and to the application thereof in the synthesis of ivabradine and addition salts thereof with a pharmaceutically acceptable acid.

More specifically, the present invention relates to a process for the synthesis of the compound of formula (I) of configuration (S):

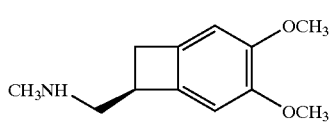

and addition salts thereof with an acid.

BACKGROUND OF THE INVENTION

The compound of formula (I) obtained according to the process of the invention is useful in the synthesis of ivabradine of formula (II):

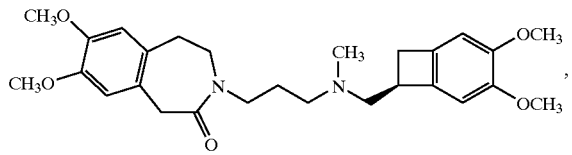

or 3-{3-[{[(7S)-3,4-dimethoxybicyclo[4.2.0]octa-1,3,5-trien-7-yl]methyl}(methyl)amino] -propyl}-7,8-dimethoxy-1,3,4,5-tetrahydro-2H-3-benzazepin-2-one, addition salts thereof with a pharmaceutically acceptable acid and hydrates thereof.

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also of various pathologies involving rhythm disturbances, especially supraventricular rhythm disturbances.

DESCRIPTION OF THE PRIOR ART

The preparation and therapeutic use of ivabradine and addition salts thereof with a pharmaceutically acceptable acid, and more especially its hydrochloride, have been described in the European patent specification EP 0 534 859.

That patent specification describes the synthesis of the compound of formula (I) by reduction of the racemic nitrile of formula (III)

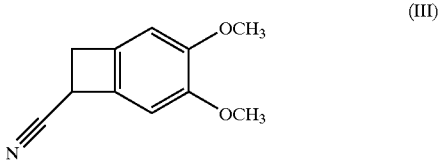

using $BH_3$ in tetrahydrofuran, followed by addition of HCl to yield the hydrochloride of the racemic amine of formula (IV):

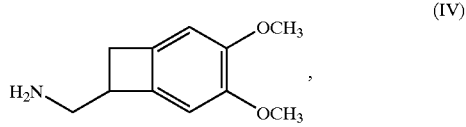

which is converted into the carbamate of formula (V):

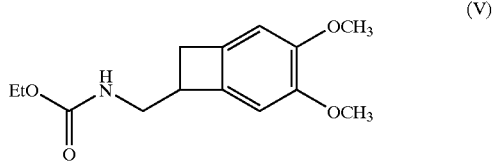

before being reduced to form the methylated amine of formula (VI):

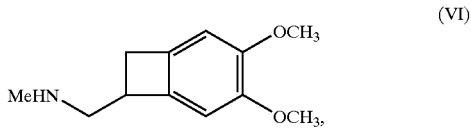

the resolution of which using camphorsulphonic acid yields the compound of formula (I).

That method has the disadvantage of yielding the compound of formula (I) in only a very low yield of from 2 to 3%.

That very low yield is due to the low yield (from 4 to 5%) of the step of resolution of the secondary amine of formula (VI).

In view of the pharmaceutical value of ivabradine and its salts, it has been imperative to be able to obtain the compound of formula (I) by an effective industrial process, and especially in a good yield and with excellent chemical and enantiomeric purities.

The Applicant has found, surprisingly, that is much more advantageous to carry out the resolution on the primary amine of formula (IV).

DETAILED DESCRIPTION OF THE INVENTION

More specifically, the present invention relates to a process for the resolution of the amine of formula (IV):

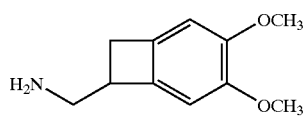
(IV)

by reaction with an optically active diacidic compound, preferably with a diacidic aminoacid compound, more preferably with N-acetyl-L-glutamic acid, followed by filtration, or filtration under suction, of the suspension thereby obtained, to yield the compound of formula (VII):

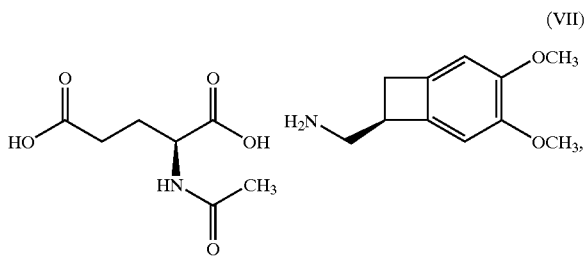
(VII)

which is reacted with a base to yield the corresponding amine of formula (VIII) of configuration (S):

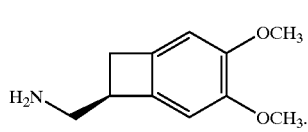
(VIII)

The reaction of the amine of formula (IV) with the diacidic compound is preferably carried out in an organic solvent, preferably an alcoholic solvent, alone or in mixture with another organic solvent, with water or with another organic solvent and water.

The base used for converting the salt of formula (VII) into the amine of formula (VIII) is preferably sodium hydroxide.

In order to improve the enantiomeric purity of the resulting compound of formula (VIII), one or more steps of recrystallisation of the compound of formula (VII) from an organic solvent, preferably an alcoholic solvent, alone or in mixture with another organic solvent, with water or with another organic solvent and water, may be added before conversion to the compound of formula (VIII).

In unexpected manner, of the resolving agents tested only a diacidic compound allowed the amine of configuration (S) to be obtained with excellent selectivity, as the following Table shows:

| Resolving agent | Nature of the acid | (S)/(R) ratio |
|---|---|---|
| (R)-camphorsulphonic acid | monoacidic | no precipitation |
| (R)-acetylphenylglycine | monoacidic | 55/45 |
| N-acetyl-D-valine | monoacidic | 55/45 |
| N-acetyl-L-leucine | monoacidic | 50/50 |
| N-acetyl-L-glutamic acid | diacidic | 93/7 |

Conditions: solvent:ethanol 95%. All the salts were heated at reflux until dissolved and allowed to recrystallise overnight.

Resolution of the amine of formula (IV) is preferably carried out in a mixture of ethanol/water or ethyl acetate/ethanol/water.

The present invention relates also to a process for the synthesis of the compound of formula (I) of configuration (S):

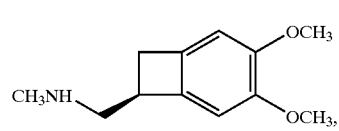
(I)

which process is characterised in that the compound of formula (III):

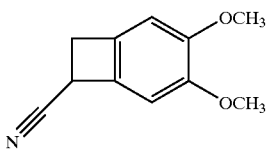
(III)

is reduced to yield the racemic amine of formula (IV), which is resolved in accordance with the process described hereinbefore to yield the optically active amine of formula (VIII), which is reacted with ethyl chloroformate to yield the optically active compound of formula (IX):

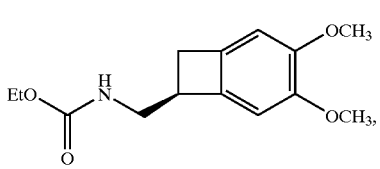
(IX)

the carbamate function of which is reduced to yield the compound of formula (I).

The addition of acid subsequently yields the corresponding salt. In particular, the addition of gaseous hydrogen chloride or HCl/ethyl acetate yields the hydrochloride of the compound of formula (I).

The hydrochloride of the compound of formula (I) is thereby obtained in an overall yield of 30% (starting from the nitrile of formula (III)), with a chemical purity of more than 98% and with an enantiomeric purity of more than 99%.

The reduction of the nitrile of formula (III) may, for example, be carried out by catalytic hydrogenation, preferably catalysed by Raney nickel, more preferably in an ammoniacal alcohol solvent such as ammoniacal methanol or ammoniacal ethanol. It may also be carried out by chemical reduction, for example using borane complexed with tetrahydrofuran or using sodium borohydride/trifluoroacetic acid.

The reaction of the optically active amine of formula (VIII) with ethyl chloroformate is preferably carried out in the presence of triethylamine or sodium hydroxide.

The reduction of the carbamate of formula (IX) is preferably carried out using an aluminium hydride such as lithium aluminium hydride or sodium bis(2-methoxyethoxy) aluminium hydride (RedAl®).

The compounds of formula (I) obtained according to the process of the present invention are especially useful as synthesis intermediates in the synthesis of ivabradine and addition salts thereof with a pharmaceutically acceptable acid.

The Example hereinbelow illustrates the invention.

EXAMPLE (1S)-4,5-Dimethoxy-1-(methylaminomethyl)-benzo-cyclobutane hydrochloride:

Step A: 4,5-Dimethoxy-1-(aminomethyl)-benzocyclobutane:

Introduce 4,5-dimethoxy-1-cyano-benzocyclobutane (6 kg), methanol (30 liters), Raney nickel (0.6 liters) and ammonia (7.32 kg) into a hydrogenator. After having purged with nitrogen and then with hydrogen, hydrogenate at 60° C. and at 30 bar until the theoretical amount of hydrogen has been absorbed. After returning to 20° C., filter off the catalyst, rinsing it with methanol, and then evaporate off the solvent. The title compound is obtained in the form of an oil, in a quantitative yield.

Step B: Addition salt of (1S)-4,5-dimethoxy-1-(aminoomethyl)-benzocyclobutane with N-acetyl-L-glutamic acid:

Introduce the compound obtained in the previous Step (10 kg), N-acetyl-L-glutamic acid (9.79 kg) and ethanol 95% (200 liters) into a reactor. Heat at reflux, with stirring, and then return to 20° C. Stir overnight at 20° C., filter off the precipitate and wash it with ethanol 95%

Recrystallisation

Introduce the salt previously obtained and ethanol 95% (80 liters) into a reactor. Heat at reflux, with stirring, and then return to 20° C. Stir overnight at 20° C., filter off the precipitate, wash it with ethanol 95% and dry it.

The title compound is collected in the form of a solid, in a yield of 40% (starting from the compound obtained in Step A) and with chemical and enantiomeric purities of more than 99%.

Step C: (1S)-4,5-Dimethoxy-1-(aminomethyl)-benzocyclobutane:

Introduce the compound obtained in the previous Step (10 kg), water (23 liters), dichloromethane (37 liters) and 3.25N aqueous sodium hydroxide solution (23 liters) into a reactor, with stirring.

After reacting at 20° C. for 30 minutes, the aqueous phase is extracted with dichloromethane. The organic phase is dried and then evaporated. The expected compound is collected in the form of an oil, in a yield of 98%.

Step D: (1S)-4,5-Dimethoxy-1-(ethoxycarbonylaminomethyl)-benzocyclobutane:

Introduce the compound obtained in the previous Step (10 kg) and dichloromethane (100 liters) into a reactor under nitrogen. Pour in, successively, triethylamine (6.17 kg) and ethyl chloroformate (5.49 liters). When all the starting material has been consumed, wash the reaction mixture with water (2×80 liters) and 1N aqueous hydrochloric acid solution (2×80 liters). Dry the organic phase, and then evaporate. The solid obtained is dried to yield the title compound.

Step E: (1S)-4,5-Dimethoxy-1-(methylaminomethyl)-benzocyclobutane:

Introduce lithium aluminium hydride (1.41 kg) and tetrahydrofuran (32.5 liters) under nitrogen into a reactor and then pour in at 20° C. a solution, in tetrahydrofuran (50 liters), of the compound obtained in the previous Step (5 kg). Heat at reflux for 1 hour and then cool to a temperature of less than 15° C. before hydrolysing the reaction mixture with water (1 liter), 5N aqueous sodium hydroxide solution (1 liter) and then water (1 liter). Filter off the solid obtained. Evaporate the organic phase. The title compound is collected in the form of an oil, in a yield of 93%.

Step F: (1S)-4,5-Dimethoxy-1-(methylaminomethyl)-benzocyclobutane hydrochloride:

Introduce the compound obtained in the previous Step (5 kg), ethyl acetate (40 liters) and ethanol (10 liters) into a reactor. Stir at 20° C. for 30 minutes and then add gaseous hydrogen chloride (1.012 kg) via an inlet in the bottom of the reactor or via an immersed tube. The suspension obtained is stirred at 15-20° C. for 1 hour and is then filtered, or filtered under suction. The precipitate is washed with a mixture of ethyl acetate/ethanol 4/1 (2×5 liters), and is then dried to yield the title compound in a yield of 92%.

We claim:

1. A process for the resolution of a compound of formula (IV):

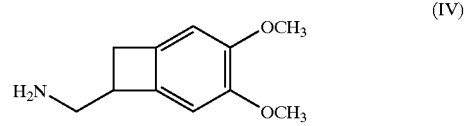

wherein the compound of formula (IV) is reacted with an optically active diacidic compound, followed by filtration, or filtration under suction, of the suspension thereby obtained, to yield a compound of formula (VII):

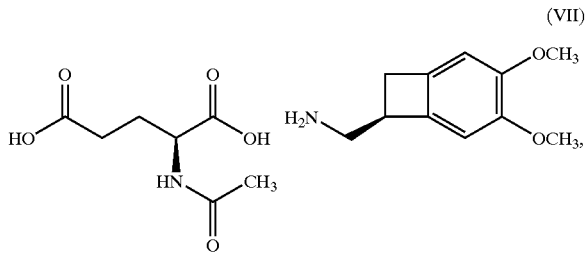

which is reacted with a base to yield a compound of formula (VIII) having configuration (S):

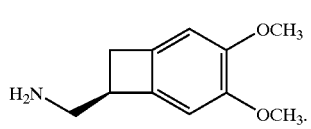
(VIII)

2. The process of claim 1, wherein the diacidic compound is a diacidic amino-acid compound.

3. The process of claim 2, wherein the diacidic amino-acid compound is N-acetyl-L-glutamic acid.

4. The process of claim 1, wherein the reaction of the compound of formula (IV) with the diacidic compound is carried out in an organic solvent, alone or in mixture with another organic solvent, with water or with another organic solvent and water.

5. The process of claim 4, wherein the reaction of the compound of formula (IV) with the diacidic compound is carried out in an alcoholic solvent, a mixture of an alcoholic solvent and water, a mixture of an alcoholic solvent and another organic solvent or a mixture of an alcoholic solvent, another organic solvent and water.

6. The process of claim 1, wherein the base used for converting the compound of formula (VII) into the compound of formula (VIII) is sodium hydroxide.

7. The process of claim 1, wherein the compound of formula (VII) is recrystallised once or more than once from an organic solvent, alone or in mixture with another organic solvent, with water or with another organic solvent and water, before being converted into the compound of formula (VIII).

8. The process of claim 7, wherein the compound of formula (VII) is recrystallised once or more than once from an alcoholic solvent, a mixture of an alcoholic solvent and water, a mixture of an alcoholic solvent and another organic solvent or a mixture of an alcoholic solvent, another organic solvent and water, before being converted into the compound of formula (VIII).

9. The process of claim 1, wherein the process is carried out in a mixture of ethanol and water or in a mixture of ethyl acetate, ethanol and water.

10. The process of claim 8, wherein the compound of formula (VII) is recrystallised once or more than once from a mixture of ethanol and water or from a mixture of ethyl acetate, ethanol and water.

11. A process for the synthesis of a compound of formula (I) of configuration (S):

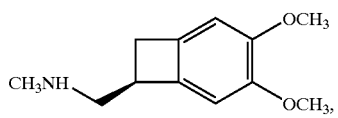
(I)

starting from a compound of formula (III):

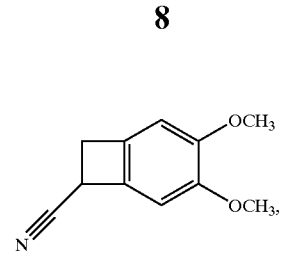
(III)

which is reduced
to yield a compound of formula (IV):

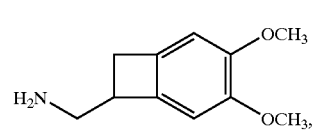
(IV)

which is resolved according to the process of claim 1, to yield the compound of formula (VIII):

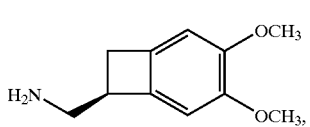
(VIII)

which is reacted with ethyl chloroformate to yield a compound of formula (IX):

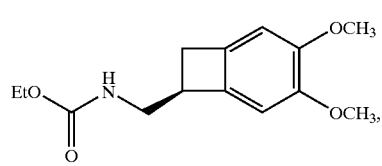
(IX)

the compound of formula (IX) thus obtained is reduced to yield the compound of formula (I).

12. The process of claim 11, wherein the compound of formula (III) is reduced by hydrogenation catalysed by Raney nickel, or by reaction with borane complexed with tetrahydrofuran or with sodium borohydride/trifluoroacetic acid.

13. The process of claim 11, wherein the reaction of the compound of formula (VIII) with ethyl chloroformate is carried out in the presence of triethylamine or sodium hydroxide.

14. The process of claim 11, wherein the compound of formula (IX) is reduced using lithium aluminium hydride or using sodium bis(2-methoxy-ethoxy)aluminium hydride.

15. A process for the synthesis of ivabradine, pharmaceutically acceptable salts thereof and hydrates thereof, starting from a compound of formula (I), wherein the compound of formula (I) is obtained according to the process of claim 11.

* * * * *